US009119923B2

United States Patent
Armitstead et al.

(10) Patent No.: US 9,119,923 B2
(45) Date of Patent: Sep. 1, 2015

(54) METHOD AND SYSTEM FOR MOTOR FAILURE DETECTION

(75) Inventors: Jeffrey Peter Armitstead, North Sydney (AU); Dion Charles Chewe Martin, Concord (AU); William Mcinnes Somerville, Hornsby (AU)

(73) Assignee: RESMED LIMITED, Bella Vista (AU)

( * ) Notice: Subject to any disclaimer, the term of this patent is extended or adjusted under 35 U.S.C. 154(b) by 1526 days.

(21) Appl. No.: 12/081,232

(22) Filed: Apr. 11, 2008

(65) Prior Publication Data

US 2008/0251071 A1    Oct. 16, 2008

Related U.S. Application Data

(60) Provisional application No. 60/907,717, filed on Apr. 13, 2007.

(51) Int. Cl.
    A61M 16/00    (2006.01)
    A62B 27/00    (2006.01)
    H02P 29/02    (2006.01)
    (Continued)

(52) U.S. Cl.
    CPC .............. *A61M 16/00* (2013.01); *H02P 29/02* (2013.01); *G01R 31/343* (2013.01); *H02K 11/001* (2013.01)

(58) Field of Classification Search
    CPC . A61M 16/0051; G01R 31/343; H02P 29/02; H02K 11/001
    USPC ............. 128/204.24, 204.21, 204.18, 202.22; 415/30; 318/400, 434; 60/431, 445
    See application file for complete search history.

(56) References Cited

U.S. PATENT DOCUMENTS

| 3,985,467 | A | * | 10/1976 | Lefferson | ......................... 417/20 |
| 5,345,158 | A | * | 9/1994 | Kliman et al. | ................ 318/434 |
| 5,546,015 | A | * | 8/1996 | Okabe | ...................... 324/765.01 |

(Continued)

FOREIGN PATENT DOCUMENTS

| JP | 01267377 | 10/1989 |
| JP | 2000141275 | 5/2000 |

(Continued)

OTHER PUBLICATIONS

Shelley (Plant Engineer, vol. 47, No. 4, pp. 10-12, Instn. Plant Eng., Jul.-Aug. 2004) and Kliman (US 6199023).*

(Continued)

*Primary Examiner* — Tan-Uyen (Jackie) T Ho
*Assistant Examiner* — Peter S Vasat
(74) *Attorney, Agent, or Firm* — Nixon & Vanderhye, P.C.

(57) ABSTRACT

Systems and methods for detecting developing faults in a flow generator or ventilator during therapeutic use thereof are provided. The motor current may be measured to estimate the torque input by the motor, while the output torque from the impeller may be determined (e.g., as inferred from the motor control system model and/or by consulting a lookup table). One or more transducers may collect data useful in determining the input and output torques. A difference between the input (to the motor) torque and the output (from the impeller) torque may be calculated. The difference, optionally filtered using a low-pass filter to reduce noise, may be compared to a predetermined threshold once or over a period of time to detect gross failures and/or developing failures. Once a failure or developing failure is detected, a user may be alerted and/or the flow generator may be placed into a "service required" mode.

28 Claims, 8 Drawing Sheets

(51) Int. Cl.
  *G01R 31/34* (2006.01)
  *H02K 11/00* (2006.01)

(56) References Cited

U.S. PATENT DOCUMENTS

| | | | |
|---|---|---|---|
| 5,563,790 A * | 10/1996 | Wada et al. | 701/41 |
| 5,671,730 A * | 9/1997 | Ollila | 128/204.21 |
| 6,199,023 B1 * | 3/2001 | Kliman | 702/67 |
| 6,591,834 B1 | 7/2003 | Colla | |
| 2004/0226561 A1 * | 11/2004 | Colla et al. | 128/204.21 |
| 2005/0031322 A1 * | 2/2005 | Boyle et al. | 388/800 |
| 2005/0252205 A1 * | 11/2005 | Stavale et al. | 60/445 |
| 2006/0038531 A1 * | 2/2006 | Wakabayashi et al. | 318/807 |

FOREIGN PATENT DOCUMENTS

| | | |
|---|---|---|
| JP | 2002-529154 | 9/2002 |
| JP | 2005-261139 | 9/2005 |
| JP | 2007-501072 | 1/2007 |
| WO | 00/27457 | 5/2000 |
| WO | 2005/016217 | 2/2005 |
| WO | 2006/047826 | 5/2006 |

OTHER PUBLICATIONS

Japanese Non-Final Office Action dated Aug. 15, 2012 for Application No. 2008-103795, with English translation (7 pages total).

Japanese Office Action, "Decision of Rejection", dated Sep. 9, 2013 for Application No. 2008-103795, with English translation (4 pages total).

First Office Action in related Japanese Application No. 2014-006621 with English translation, dated Dec. 22, 2014, 8 pages.

Japanese Office Action, "Decision of Rejection," issued in Japanese Patent Application No. 2014-006621, dated Jun. 8, 2015, along with its English language Translation (8 pages).

* cited by examiner

METHOD AND SYSTEM FOR MOTOR FAILURE DETECTION

CROSS-REFERENCE TO RELATED APPLICATION

This application claims the benefit of Application Ser. No. 60/907,717 filed on Apr. 13, 2007, the entire contents of which is hereby incorporated herein by reference.

FIELD OF THE INVENTION

The example embodiments disclosed herein relate to systems and/or methods for motor failure detection in mechanical devices, e.g., devices suitable for treating respiratory insufficiency/failure and/or sleep-disordered breathing (SDB), such devices implementing, for example, non-invasive techniques (using, for example, mask systems, flow generators or ventilators, positive airway pressure (PAP) devices, etc.) and/or invasive ventilation, volume modes, mechanical ventilation, and/or other like techniques. More particularly, the example embodiments disclosed herein relate to systems and/or methods that detect developing motor failures by comparing the input torque and output torque of a flow generator/ventilator.

BACKGROUND OF THE INVENTION

Obstructive Sleep Apnea (OSA) and other dangerous sleep-disordered breathing (SDB) conditions affect thousands worldwide. Numerous techniques have emerged for the treating SDB, including, for example, the use of Continuous Positive Airway Pressure (CPAP) devices, which continuously provide pressurized air or other breathable gas to the entrance of a patient's airways via a patient interface (e.g. a mask) at a pressure elevated above atmospheric pressure, typically in the range 3-20 cm $H_2O$. Typically, patients suspected of suffering from SDB register with a certified sleep laboratory where sleep technicians fit patients with numerous data collectors and monitor their sleep activity over a given period. After the patient is diagnosed, a treatment regimen usually is developed, identifying both a treatment apparatus (or treatment apparatuses) and program of use for the treatment apparatus(es).

FIG. 1 shows a simplified schematic of a typical CPAP treatment apparatus. An impeller 1 is powered by an electric motor 2 using a servo 3 under the direction of a microprocessor-based controller 4. The supply of breathable gas is carried to the mask 5 through a flexible conduit 6. The apparatus has various switches 7, displays 8, and a number of transducers. The transducers may monitor a number of processes, such as, for example volumetric flow rate 10 (e.g., at a predetermined point in the flow path), pressure 11 (e.g., at a predetermined point downstream of the flow generator outlet or at the mask), snore 12, flow generator rotational speed 13, and/or motor parameters 14.

It would be advantageous to detect faults in the treatment apparatus as they develop during the operation of the blower. A gross failure of a motor bearing and/or turbine results in the patient ceasing to receive treatment. However, if a motor bearing and/or turbine begin(s) to fail, a patient may receive sub-optimal treatment for the period of time between the beginning of the failure and when the failure is complete. A failing motor may result in low (or lower than expected) pneumatic output. Failing to recognize developing faults also may cause the bearing to overheat, which may, in turn, result in a potential hazards.

To this end, U.S. Pat. No. 5,621,159, the entire contents of which is incorporated herein by reference, discloses techniques for determining increased rotational friction. Unfortunately, further improvements to these techniques are necessary, as they require powering down the fan for a predetermined period to check the spin-down rate, which makes such techniques inappropriate for flow generators actually in use.

Certain other techniques for detecting faults are described in AU 764761, and U.S. Pat. Nos. 6,591,834, 6,745,768, and 7,040,317, the entire contents of each of which is hereby incorporated herein by reference. Further improvements to these techniques also would be advantageous, as there are certain faults that cannot be detected using such techniques. For example, such techniques generally cannot determine whether there is a faulty bearing that is not yet causing a "motor stalled" condition or a near-motor-stalled condition. It would be advantageous to detect other failures, such as, for example, low output torque, increased bearing friction, constricted inlet(s), faulty or disconnected Hall sensor(s), etc.

Thus, it will be appreciated that there is a need in the art for improved motor fault detection techniques.

SUMMARY OF THE INVENTION

One aspect of certain example embodiments relates to a holistic approach to detecting faults in a flow generator. Such faults may include, for example, degraded bearings, a failing motor, low output torque, increased bearing friction, constricted inlet(s), dropped phase, disconnected Hall sensor(s), rubbing/loose/fragmented impeller, etc.

Another aspect of certain example embodiments relates to comparing the expected and monitored load torque of a flow generator, with the expected load torque being known beforehand and specific to a particular flow generator (or model of flow generators), and the monitored load being calculated and/or inferred from a model and/or lookup table.

Still another aspect of certain example embodiments relates to techniques for detecting faults in a flow generator without suspending operation of the flow generator.

Yet another aspect of certain example embodiments relates to techniques for detecting developing faults in a flow generator.

The techniques of certain example embodiments can be applied to any device having a motor (e.g., with a bearing) to detect faults therein by, for example, comparing the useful (output) torque produced by the system with the (input) torque generated by the motor. These techniques may be used for motor testing and/or fault detection (e.g., gross fault detection, developing fault detection, and the like) before the motor is incorporated into the device, as a diagnostic function of an assembled device, etc.

In certain example embodiments, a method is provided to detect developing faults in a flow generator during therapy. A flow generator may employ an impeller powered by a motor under servo control. The torque exerted on the impeller by the fluid load is estimated from measured parameters. This is the output (e.g., useful) torque. The motor torque (e.g., input motor torque) can be determined in part from motor current. A difference between the input torque and the output torque may be calculated. The determination of whether a fault exists may be based at least in part on an assessment of the difference. The term expected motor torque alternatively may be used to signify the torque that is exerted on the impeller expected from the measured outputs from the turbine, including, for example, measured pressure, flow, and/or rotational speed.

In certain other example embodiments, a turbine-based ventilator device is provided. An impeller may be powered by a motor under servo-control. The system's servo-controller may be further configured to indicate the presence of developing faults of the turbine-based ventilator device during therapeutic use of the turbine-based ventilator device based on a comparison of useful output torque (e.g., based on measured parameters) and the input (e.g., motor) torque. The turbine-based ventilator device may be a flow-target, volume-target, or pressure-target device, in certain example embodiments. Also, the turbine-based ventilator device may be a PAP device in certain example embodiments.

Optionally, the difference may be filtered to reduce noise. The difference, filtered or unfiltered, may be used to assess whether a fault exists, based on, for example, a comparison (or comparisons) with at least one predetermined threshold. It will be appreciated that certain example embodiments described herein may be in connection with the treatment of SDB (e.g., OSA) via non-invasive (e.g., mask) ventilation and/or positive airway pressure devices. However, certain example embodiments may be used in connection with invasive ventilation techniques, volume modes, and/or beyond SDB to mechanical ventilation in general. By way of example and without limitation, such techniques may be applicable whenever the safe operation with oxygen is a concern, which often is the case in general ventilation.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

1. Fault Detection

Figure 1:
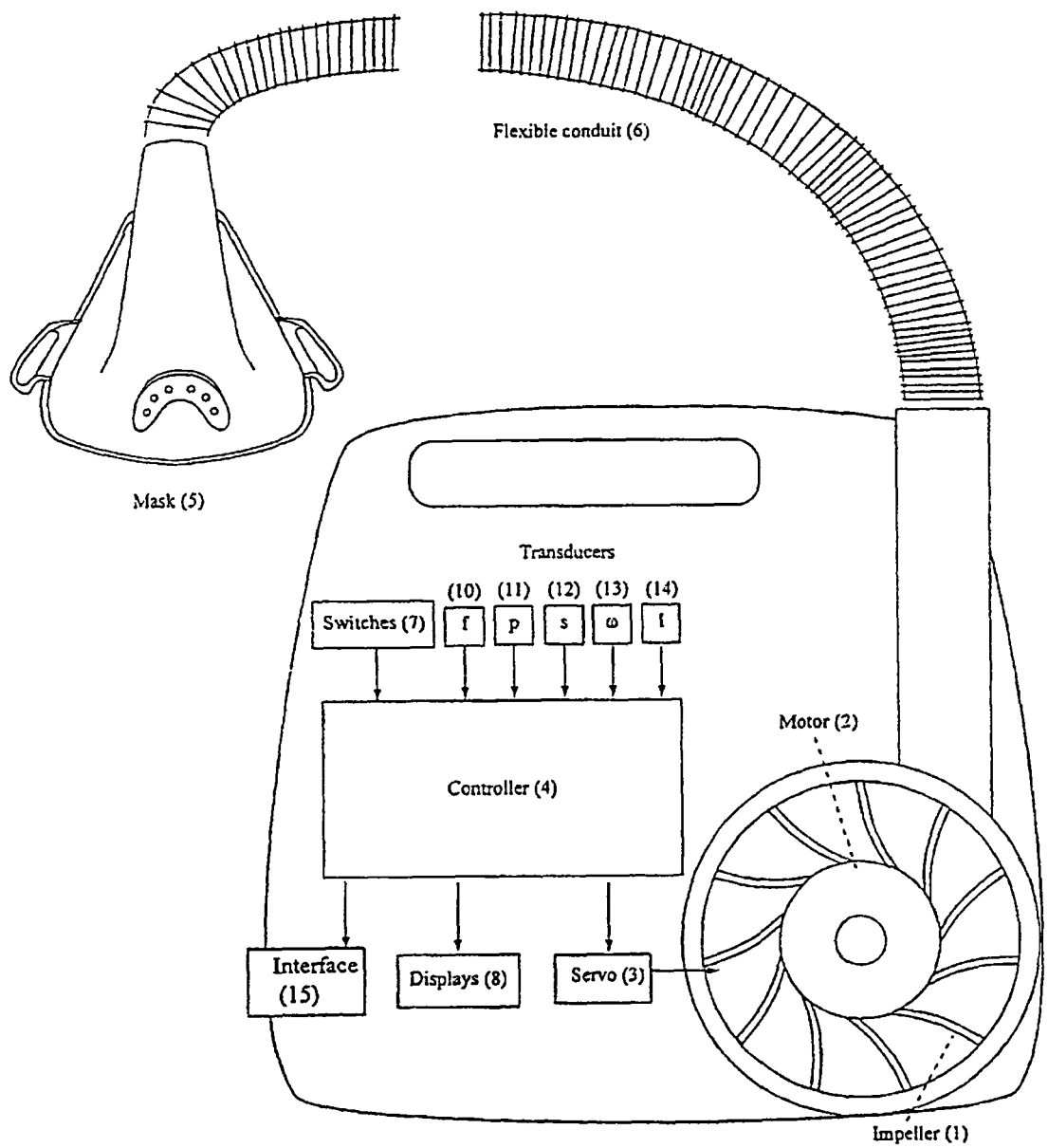
FIG. 1 shows a simplified schematic of a typical CPAP treatment apparatus.

Certain example embodiments relate to techniques for detecting developing faults in flow generators. This may be made possible by calculating the difference between the expected and monitored load torques of a flow generator. The difference, filtered or unfiltered, may be compared to one or more predetermined thresholds (e.g., over a period of time) to determine whether a gross fault has occurred and/or whether a fault is developing. The following sections detail illustrative equations and illustrative hardware/software configurations that may be used in conjunction with this approach.

1.1 Model Overview

The blower is powered by a motor 2 that delivers a torque to the impeller 1 which accelerates the delivered fluid. At any point in time, there will be a balance between the torque developed by the motor and the torque required for accelerating the fluid, accelerating the mass of the impeller and motor rotor, and any losses in the system. It will be appreciated that this balance also could be formulated in terms of power. The torque developed by the motor can be calculated from the current consumed by the motor by applying the motor constant $k_m$. For a multiphase motor, this constant will be a per-phase equivalent constant. The torque provided by the motor is then:

$$T_m = k_m \cdot I_m,  \quad (1)$$

where $I_m$ is the motor current. This torque is balanced by the torques detailed above as in the equation:

$$T_m = \frac{p \cdot Q}{\omega} + J \frac{\partial \omega}{\partial t} + T_{loss}, \quad (2)$$

where p is the pressure delivered to the patient in Pascals (or the difference in pressure between the outlet and inlet of the impeller if the inlet pressure is not zero), Q is the flow-rate in $m^3 \cdot s^{-1}$ of the delivered gas, $\omega$ is the rotational speed of the impeller in radians per second (which may be measured directly or indirectly, e.g., as some brushless DC or "sensor-less motors" are capable of inferring rotational speed from back-emf), J is the rotational moment of inertia of all the spinning mass that the motor is accelerating, and $T_{loss}$ is the sum of all the loss torques. The last term in equation (2) can be modeled, for example, using the following function:

$$T_{loss} = T_{cons} + f(p, Q^2, \omega). \quad (3)$$

It will be appreciated that here, the density, viscosity, and temperature of the fluid are assumed to be constant. When this is not true, certain example embodiments may allow constants to be incorporated to allow for measured and/or inferred changes in these and/or other variables. The rationale for this last equation is as follows. $T_{cons}$ represents a "constant torque load" typical of rotating machinery. A torque proportional to $\omega$ is a viscous torque attributable to fluid-filled ball bearings. A torque term proportional to the pressure across the impeller will account for leakage from high pressure zones to low pressure zones, and a torque proportional to $Q^2$ will allow for the (mostly turbulent) losses along the fluid path of the impeller and housing. In certain example embodiments, the function $f$ may be assumed to be approximately linear, although the present invention is not so limited. For example, in certain other example embodiments, the function $f$ may be nonlinear, a lookup table, etc. One example of a suitable function is:

$$T_{loss} = T_{cons} + k_1 \cdot \omega + k_2 \cdot Q^2 + k_3 \cdot p. \quad (4)$$

For the purposes of the discussion herein, SI units will be used, implying that torque will be measured in Newton-meters. Of course, it will be appreciated that other units of measurement can be used in other example embodiments.

Certain example embodiments relate to a therapy device having a motor and an impeller as above, transducers suitable for measuring and/or calculating p, Q, $\omega$, $I_m$. Such capabilities allow the torque balance in equation (2) to be monitored. For example, when the difference between the left-hand-side term and the sum of the right-hand-side terms exceeds a predetermined threshold, a signal may be generated to indicate that service is necessary (e.g., an audible alarm and/or visual alarm may be triggered, the flow generator may be placed into a "requires service" mode, etc.). As another example, the balance can be tracked over time to give an indication of expected remaining service life or "health status." It will be appreciated that the term related to rotational inertia $$\left(J\frac{\partial \omega}{\partial t}\right)$$

could be ignored if the torque balance were only checked during non-acceleration periods.

Thus, in certain example embodiments, the predetermined threshold may be indicative of a value signifying a gross failure, whereas the predetermined threshold may be indicative of a relative (e.g., growing) failure in certain other example embodiments. Certain example embodiments may be capable of indicating both gross failures (e.g., a single difference being above a given threshold), as well as relative failures (e.g., increasing differences between the monitored and expected torques beyond a threshold indicative of an acceptable increase). The predetermined threshold may be expressed in terms of an absolute value, a percentage increase or decrease, etc.

1.2 Calculation of $T_m$

Equation (1) shows that the torque provided by the motor can be calculated as the product of the motor current and the motor torque constant. Ordinarily, the motor torque constant will be provided by the motor manufacturer. The motor supply current then only needs to be measured or inferred to complete input to this equation. Accordingly, if a low-valued resistor is placed in line between the power supply and the motor, then the voltage across that resistor will be approximately linearly proportional to the current supplied to the motor. Also, if the motor is controlled using switched-mode technology, then the voltage across the resistor may need to be filtered to provide a substantially noise-free estimate of supply current.

Figure 2:
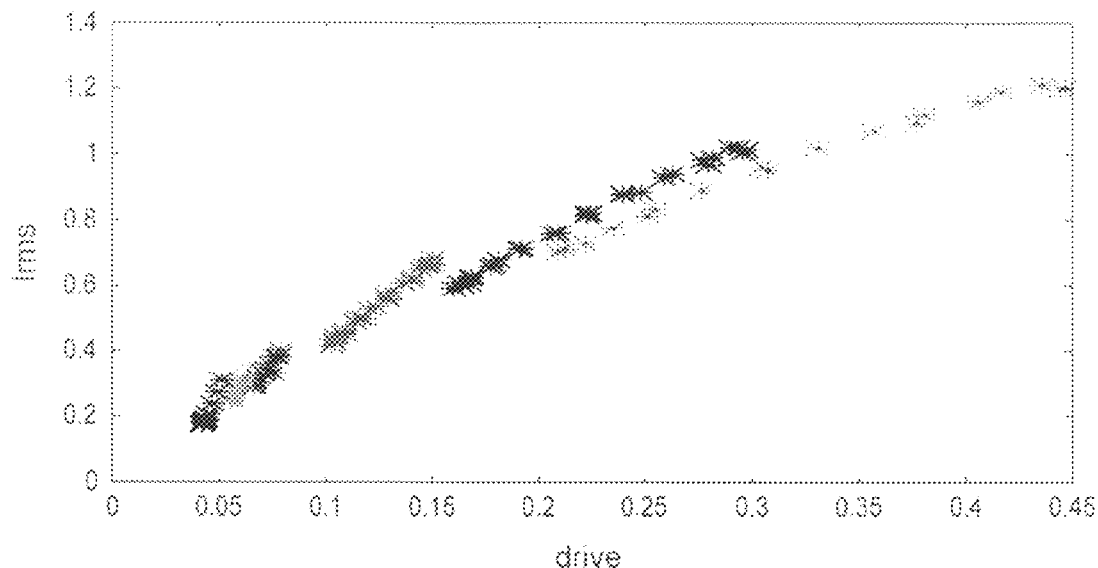
FIG. 2 shows the relationship between drive and the r.m.s. supply current for six different constant angular velocities experimentally obtained from an AutoSet CS2 blower, which is commercially available from ResMed.

The motor supply current also can be inferred from other parameters involved in the closed-loop control of motor current. For example, a transconductance amplifier can be used to control motor current in a closed loop fashion. Here, a control voltage, known as "drive," is the input to the transconductance amplifier that uses switch-mode technology to control the current fed to the motor. At a substantially constant angular velocity of the motor, there will be an almost-linear relationship between the control voltage "drive" and the motor supply current. FIG. 2 shows the relationship between drive and the r.m.s. supply current for six different constant angular velocities experimentally obtained from a AutoSet CS2 blower, which is commercially available from ResMed. The plots correspond, from left to right, to RPMs of 5,000; 8,000; 10,000; 15,000; 20,000; and 23,000.

Figure 3:
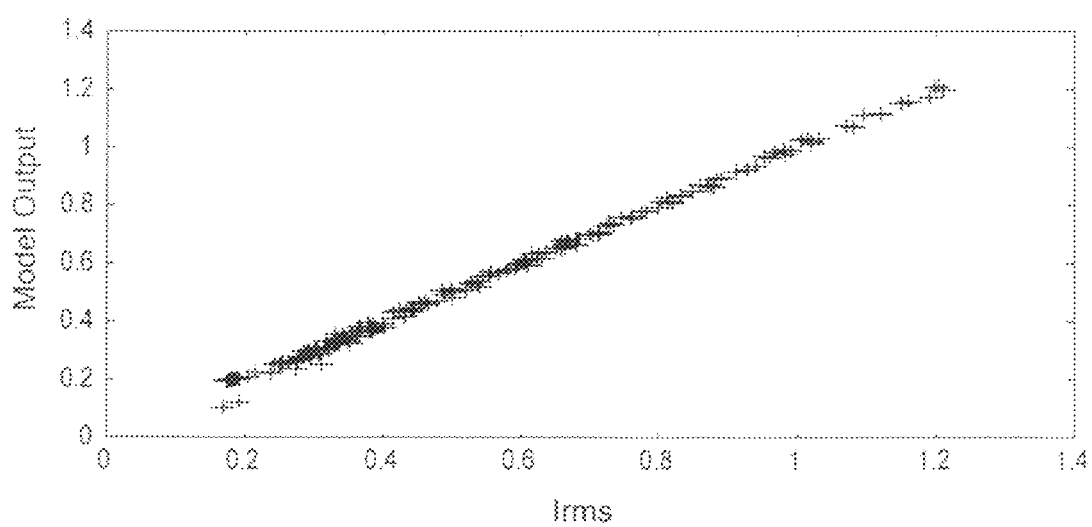
FIG. 3 shows the results of modeling the r.m.s. current as a nonlinear function of drive and angular velocity.

The change in the relationship between drive and supply current with angular velocity can be accommodated by a model or lookup table that covers the required operating range. Because the transconductance amplifier loop may run at a very high speed (e.g., about 20 kHz), the model or lookup table can be created using static tests (e.g., tests at a substantially constant velocity), but the results will still be valid generally for a dynamically changing system (e.g., where the motor is accelerating). FIG. 3 shows the results of modeling the r.m.s. current as a nonlinear function of drive and angular velocity. The plot represents the same data as those plotted in FIG. 2 and displays a substantially linear relationship between modeled and real r.m.s. current. The slope of the line is approximately one, the y-intercept is about zero, and the correlation coefficient is about 0.998. It will be appreciated that this model could also be implemented by a lookup table.

1.3 Calculation of the Torque Required to Accelerate the Breathable Gas

The power produced by a pump is equal to $p \cdot Q$, where, if p is measured in Pascals and Q in $m^3 \cdot s^{-1}$, the result will have units of Watts. If the power produced by the pump is divided by the angular velocity in radians per second, the result is torque in Newton-meters. If the pump is 100% efficient (e.g., no fluid or mechanical losses), then this torque is that required of the motor when the pump is turning at constant angular velocity.

1.4 Calculation of the Torque Required to Accelerate the Spinning Mass of the Pump and Motor Rotor and Shaft If the motor and pump are accelerating (e.g., the angular velocity is not constant), then a torque will be required to accelerate the combined spinning mass as:

$$T_{inertia} = J\frac{\partial \omega}{\partial t}, \quad (5)$$

where J has the SI units of $kg \cdot m^2$, $T_{inertia}$ has units of Newton-meters, and $$\frac{\partial \omega}{\partial t}$$

has units of $(radian) \cdot s^{-2}$.

For the AutoSet CS2 blower, the value of J is $2 \cdot 1.13 \, E^{-6}$ (two impellers)$+1.26 \, E^{-7}$ (motor)$=2.386 \, E^{-6} \, kg \cdot m^2$.

1.5 Calculation of the Torque Consumed by the Bearings and Pump Inefficiencies

As noted above, the inefficiencies of the pump and losses related to the bearings can be modeled empirically while still basing the functional principles of certain example embodiments on sound physical principles. One such model is $$T_{loss} = T_{cons} + k_1 \cdot \omega + k_2 \cdot Q^2 + k_3 \cdot p. \quad (6)$$

Here, $T_{cons}$ represents the static or Coulomb friction of the bearings, and $k_1$ represents the viscous friction typical of grease-filled bearings. $k_2$ represents the (predominantly turbulent) fluid losses within the pump housing, and $k_3$ represents losses related to leakage from high pressure zones to low pressure zones.

Typical values of the constants above for a AutoSet CS2 blower are $T_{cons} = 5.4721 E^{-4} \, N \cdot m$
$k_1 = 1.8838 E^{-6} \, N \cdot m \cdot (radian^{-1}) \cdot s$
$k_2 = 1.2585 E^2 \, N \cdot m^{-5} \cdot (radian^{-1}) \cdot s^2$
$k_3 = 1.0493 E^{-7} \, N \cdot m \cdot Pa^{-1}$ These values were calculated using a "known-good" unit and a least squares fitting routine. It will be appreciated that constants for other units may be calculated using the same or similar techniques.

1.6 An Example of Dynamically Calculated Torque Difference

Figure 4:
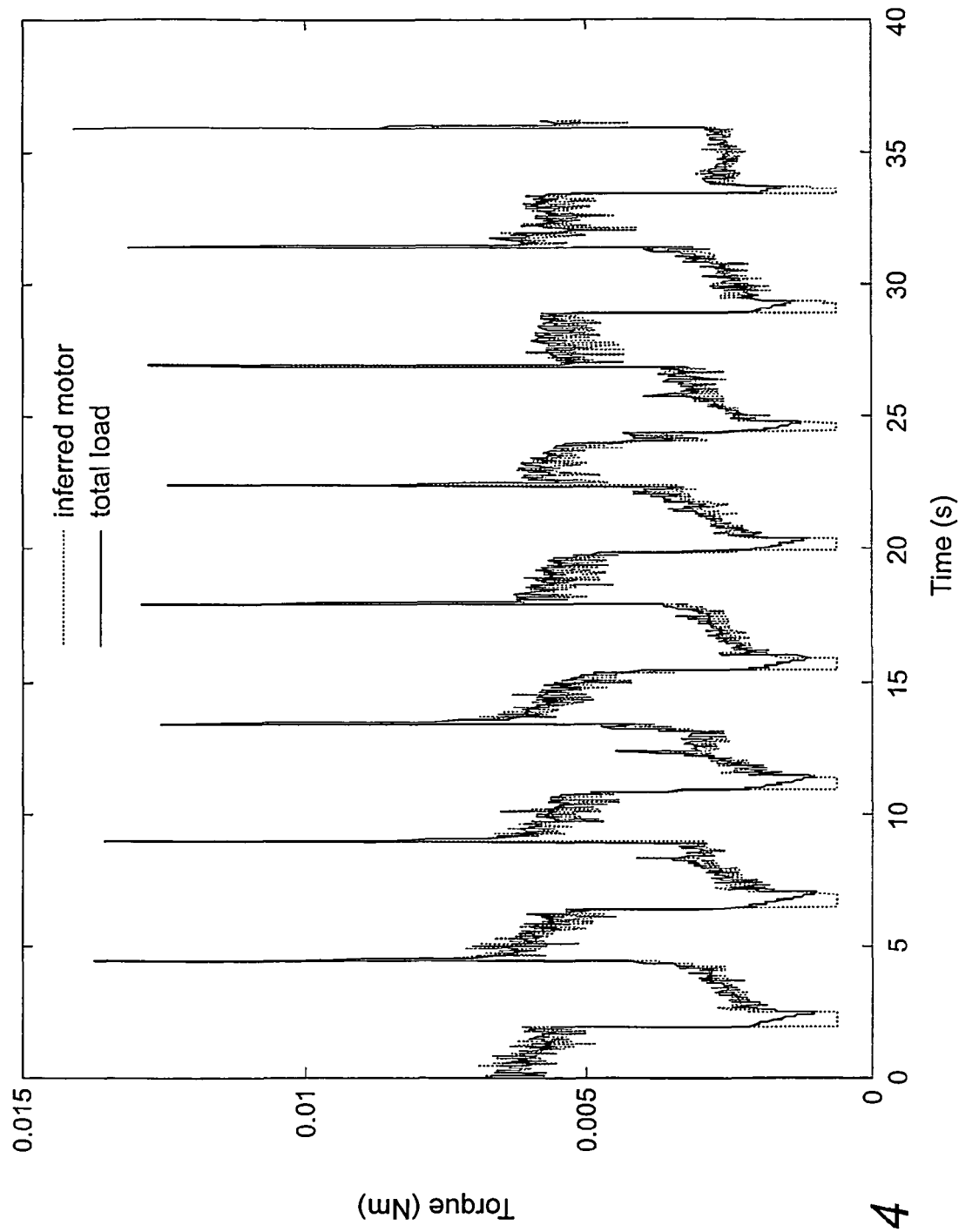
FIG. 4 shows two plots of torque in Newton-meters vs. time.

FIG. 4 shows two plots of torque in Newton-meters vs. time, the dotted curve being that supplied by the motor and the solid curve being that related to the combined load. The AutoSet CS2 blower is here delivering pressure in simple bilevel fashion with a fixed cycle length while a subject breathes. The motor torque was calculated using the model developed with static tests, e.g., $$T_m = f(drive, \omega). \quad (7)$$

It will be appreciated that motor current also can be calculated as a function of drive (representing the [0, 1] signal output by the motor controller) and speed of the motor spindle, as modeled by the equation $T_m = f(\text{drive, RPM})$.

Figure 5:
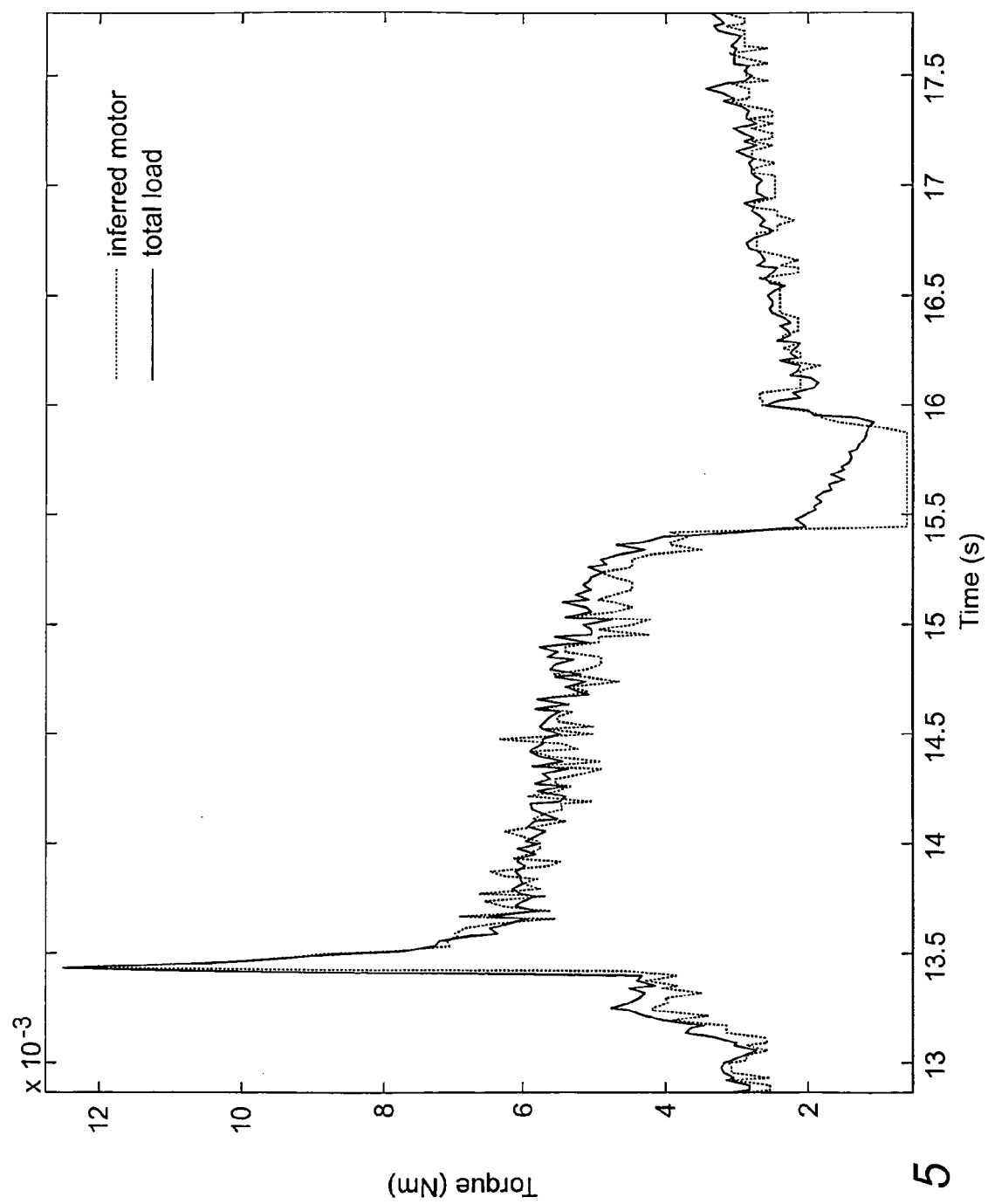
FIG. 5 shows a close-up of one cycle in FIG. 4.
Figure 6:
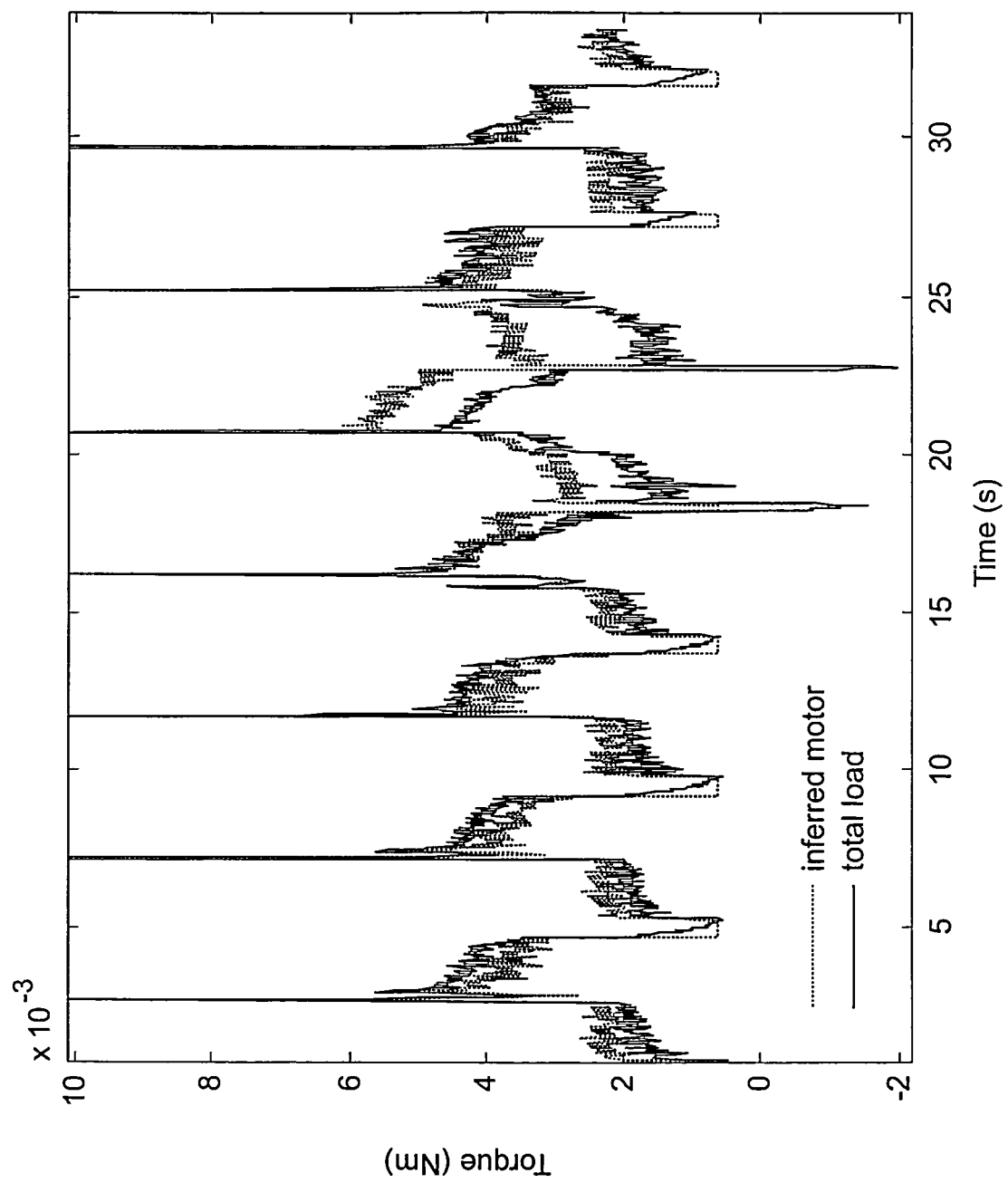
FIG. 6 shows the same scenario, this time with a perturbation of the load torque between 15 and 25 seconds.
Figure 7:
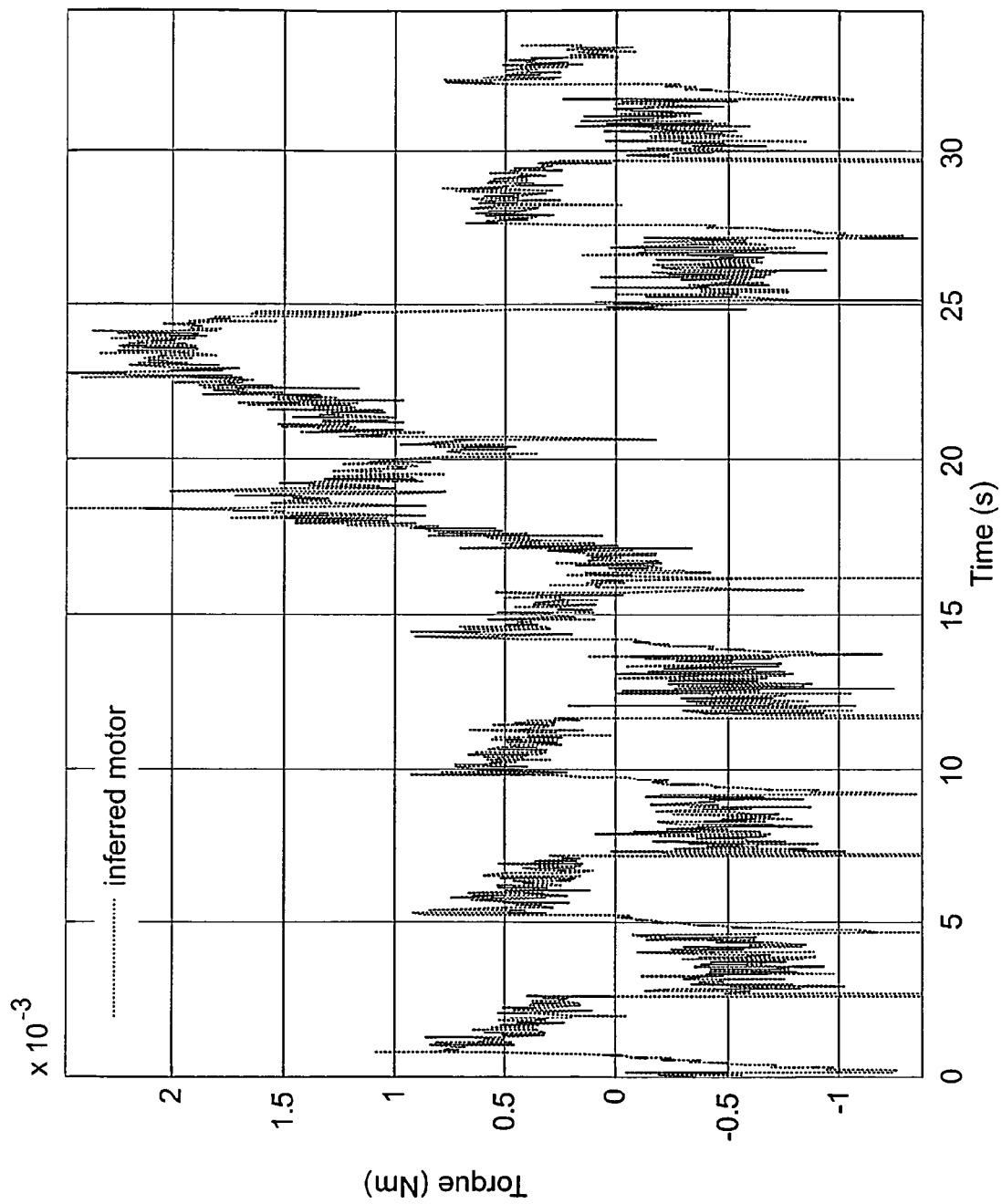
FIG. 7 shows the expected torque difference.

FIG. 5 shows a close-up of one cycle in FIG. 4, showing good correspondence (e.g., torque balance) between the two signals. FIG. 6 shows the same scenario, this time with a perturbation of the load torque between 15 and 25 seconds. The perturbation included a small amount of friction being applied to the impeller surface. As will be appreciated from FIG. 6, the motor torque curve is shifted up during the perturbation, e.g., the motor is supplying some "extra" torque not matching the expected load. FIG. 7 shows the expected torque difference, and again there is a pronounced difference in the balance during the perturbation.

2. An Example of Longer-Term Monitoring of Blower "Health" Status

Figure 8:
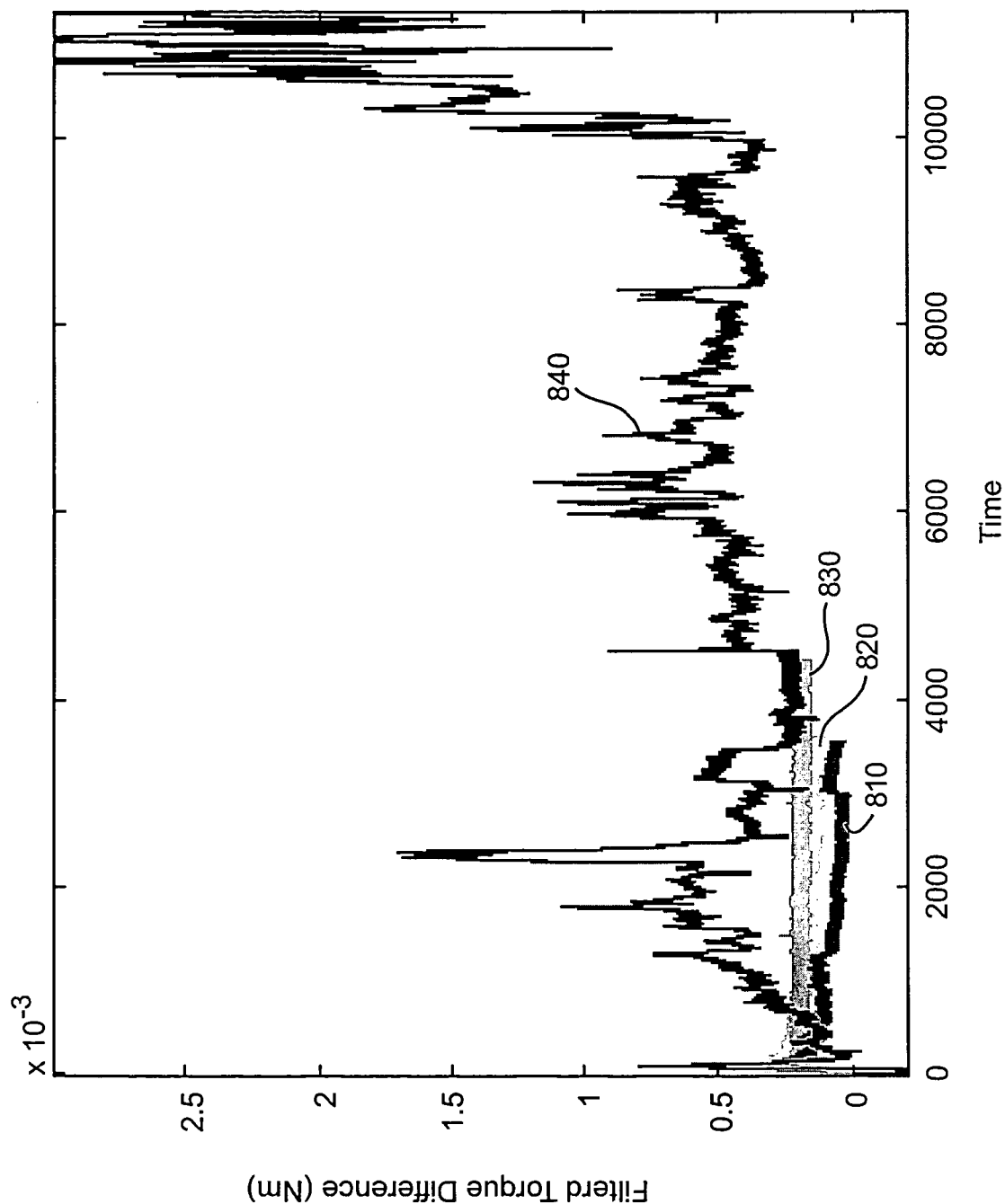
FIG. 8 shows longer-term monitoring of the torque-balance trace in FIG. 7 for four separate units; and, FIG. 9 is an illustrative flowchart showing a fault detection method, in accordance with an example embodiment.

FIG. 8 shows longer-term monitoring of the torque-balance trace in FIG. 7 for four separate units. In FIG. 8, the displayed traces have been filtered with a time constant of 100 seconds to eliminate transient noise. Three "good" units (curves 810, 820, and 830) were run for around one hour and displayed similar near-zero torque difference. A fourth crippled unit (curve 840) was run for about three hours until bearing failure. This unit had had the grease removed from its bearing at time zero and at the one hour point some dust was introduced into the bearing. The crippled unit clearly displays a greatly increased torque difference, indicating that the motor is supplying torque (or power) to an "unexpected" load. It will be appreciated that this unit could have been shut down by the controlling software long before catastrophic failure based at least in part on the detection of the large filtered torque difference.

3. Illustrative Flowchart Showing Fault Detection Example Methods

Figure 9:
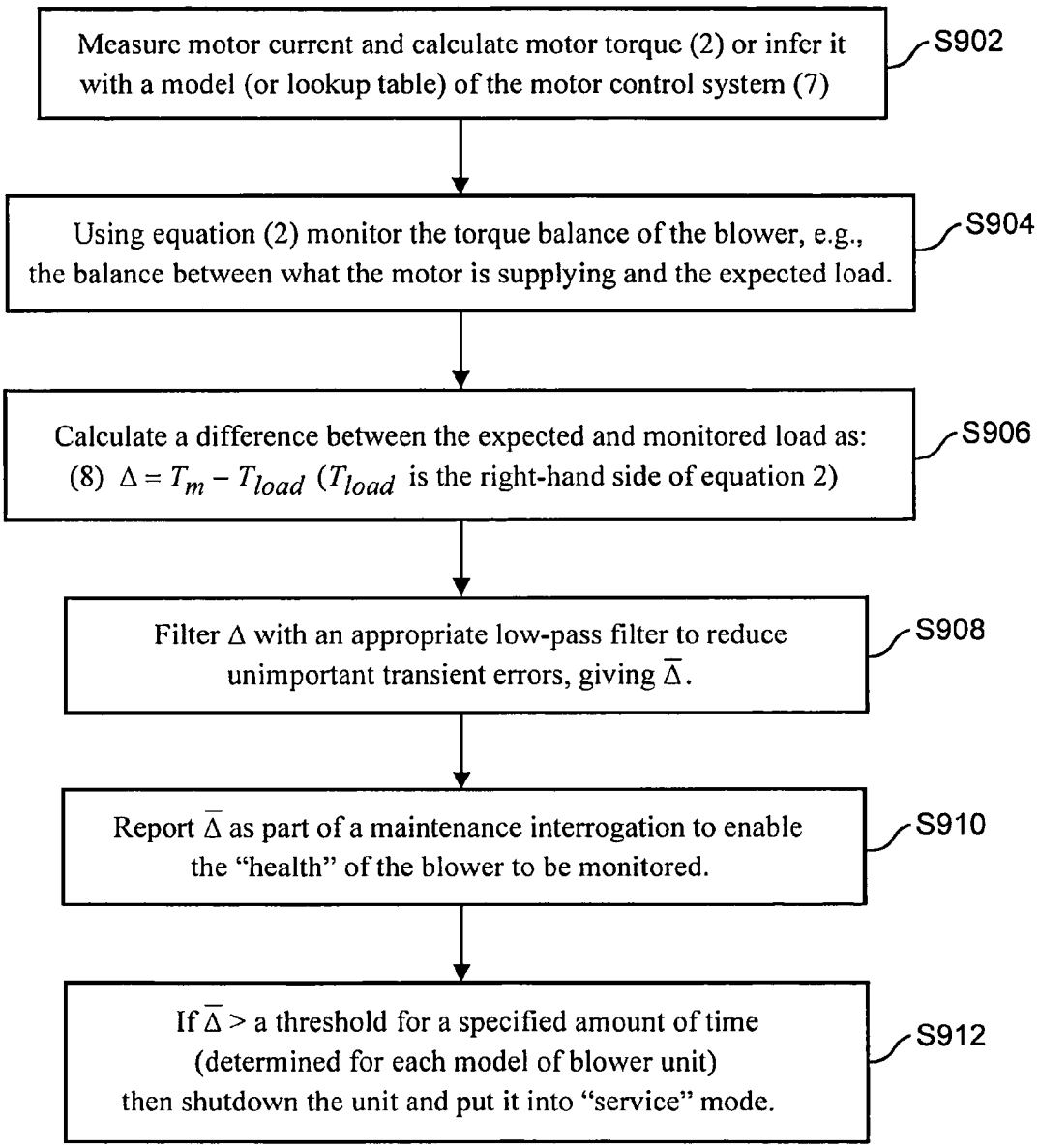

FIG. 9 is an illustrative flowchart showing a fault detection method, in accordance with an example embodiment. In step S902, the motor current is measured, and the motor torque is determined. The motor torque can be calculated, for example, using equation (2). Alternatively, the motor torque can be inferred using a model and/or lookup table of the motor control system, for example, using equation (7). In step S904, the torque balance (e.g., the balance between what the motor is supplying and the expected load) of the blower is monitored, for example, using equation (2). The difference between the expected and monitored (actual) load may be calculated in step S906. The difference may be modeled as:

$$\Delta = T_m - T_{load}, \tag{8}$$

with $T_{load}$ being the right-hand side of equation (2).

In step S908, $\Delta$ may be filtered with an appropriate low-pass filter to reduce unimportant transient errors, producing $\overline{\Delta}$. In step S910, $\overline{\Delta}$ may be reported as part of a maintenance interrogation (e.g., by the controller 4 and output via one or more displays 8), reflecting the "health" of the flow generator. As shown in step S912, if $\overline{\Delta}$ is greater than a predetermined threshold for a specified amount of time, the flow generator may be shutdown, put into a "service mode," and/or may otherwise alert a user that a fault is detected and/or anticipated. It will be appreciated that the predetermined threshold and/or the amount of time may be particular to the model of the flow generator being used.

The monitoring and/or calculating processes may be performed and/or aggregated over a longer period of time. This data may be stored (e.g., to a memory) and compared for longer-term trending purposes to measure the overall health of the flow generator and/or changes to the overall health of the flow generator. For example, the actual performance may be compared to an idealized performance over a longer period of time. Significant deviations from the idealized performance may be indicative of a problem with the flow generator and/or the monitoring equipment.

It will be appreciated that although certain example embodiments have been described in relation to a CPAP device and/or to ResMed's AutoSet CS2 model blower, the present invention is not so limited. Instead, the example embodiments described herein may be used in conjunction with other types of flow generators (e.g., PAP devices generally, bilevel devices, AutoSet algorithm devices, etc.), potentially available from any manufacturer. Also, it will be appreciated that the hardware components described herein are not limited to any particular arrangement. For example, the transducers may be a part of a particular flow generator, they may be part of a separate module to be integrated into a particular flow generator, they may be separate from a particular flow generator, etc. Moreover, it will be appreciated that the hardware and/or software components described herein may comprise any combination of hardware, software, firmware, or the like that provides suitable functionality. For example, the calculations may be implemented by software algorithms executable and/or embedded into the controller 4.

One advantage of certain example embodiments relates to patients benefiting from increased safety and the knowledge of impending failure(s). Another advantage of certain example embodiments relates to developing fault detection without the need for temperature and/or other sensors, as enabled by, for example, software algorithms transforming data already monitored by hardware elements of the treatment apparatus. The detectable faults may include, for example, degraded bearings, a failing motor, low output torque, increased bearing friction, constricted inlet(s), dropped phase, disconnected Hall sensor(s), impeller failures, etc.

It will be appreciated that although certain example embodiments have been described as relating to PAP devices and/or flow generators, the present invention is not limited to any particular device. For example, the example embodiments described herein may be used in connection with any suitable turbine-based ventilator. Such turbine-based ventilators may include, for example, flow, volume, and/or pressure target based devices. Such turbine-based ventilators also may include, for example, traditional mechanical ventilators, CPAP devices, high-flow nasal cannula based devices, etc.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments.

Also, the various embodiments described above may be implemented in conjunction with other embodiments, e.g., aspects of one embodiment may be combined to provide treatment in connection with invasive ventilation techniques, volume modes, mechanical ventilation, etc. In addition, while the invention has particular application to patients who suffer from OSA, it is to be appreciated that patients who suffer from other illnesses (e.g., ventilatory insufficiency or failure, congestive heart failure, diabetes, morbid obesity, stroke, bariatric surgery, etc.) can derive benefit from the above teach-

What is claimed is:

1. A method of detecting developing faults in a flow generator having an impeller powered by a motor under servo-control during therapeutic use of the flow generator, the method comprising:
supplying a flow of pressurized breathable gas generated by the flow generator;
measuring, with a first transducer, a motor current supplied to the motor when the flow generator is generating the flow of pressurized breathable gas;
determining, with a controller having a processor, an input motor torque value generated by the motor, the input motor torque value based at least in part on the motor current measured by the first transducer;
measuring, with a second transducer, at least one output from a turbine of the motor;
determining, with the controller, a load motor torque value, the load motor torque value based at least in part on the at least one measured output measured by the second transducer;
calculating, with the controller, a difference between the load motor torque value and the input motor torque value, the difference being associated with losses in the motor; and
assessing, with the controller, whether a fault is developing in the flow generator based at least in part on the difference by comparing the difference to a predetermined threshold.

2. The method of claim 1, wherein the determination of the input motor torque value with the controller is further based on an inference from a motor control system model.

3. The method of claim 1, wherein the determination of the input motor torque value with the controller is further based on a motor control system lookup table.

4. The method of claim 1, further comprising activating an alert and/or placing the flow generator into a service required mode when development of a fault has been assessed by the controller.

5. The method of claim 1, further comprising indicating development of a fault with an audible alarm and/or a visual alarm when the difference calculated by the controller exceeds the predetermined threshold for a specified amount of time.

6. The method of claim 1, further comprising filtering the difference with a low-pass filter.

7. The method of claim 6, wherein the low-pass filter is configured to reduce transient errors.

8. The method of claim 6, further comprising comparing the filtered difference to the predetermined threshold.

9. The method of claim 8, further comprising indicating development of a fault with an audible alarm and/or a visual alarm when the filtered difference calculated by the controller exceeds the predetermined threshold for a specified amount of time.

10. The method of claim 1, further comprising correcting for variations in one or more of ambient pressure, temperature, and viscosity with the controller.

11. The method of claim 1, wherein the at least one measured output includes pressure, flow, and/or rotational speed.

12. A turbine-based ventilator device to supply a flow of pressurized breathable gas, comprising:
a motor configured to drive an impeller to generate the flow of pressurized breathable gas to be supplied;
a first transducer configured to measure motor current supplied to the motor while the motor is generating the flow of pressurized breathable gas;
at least one additional transducer configured to measure at least one output from a turbine of the motor; and,
a closed-loop controller configured to control the motor,
wherein the controller is further configured to detect a developing fault of the device during therapeutic use of the device, the developing fault being detected based on a comparison of an input motor torque value and a load motor torque value, and
wherein the input motor torque value is based at least in part on the motor current measured by the first transducer, and
wherein the load motor torque value is based at least in part on the at least one measured output measured by the at least one additional transducer.

13. The device of claim 12, further comprising a flexible conduit connected to a patient interface, the conduit and the patient interface being suitable for conveying a supply of pressurized breathable gas to the patient.

14. The device of claim 12, wherein the first transducer comprises a transconductance amplifier configured to measure motor current.

15. The device of claim 12, wherein the at least one output includes at least one of: pressure delivered to a patient, flow, rotational speed of the impeller, and motor current.

16. The device of claim 12, wherein the input motor torque value is further based, at least in part, an inference from a motor control system model.

17. The device of claim 12, wherein the input motor torque value is further based, at least in part, a motor control system lookup table.

18. The device of claim 12, further comprising a low-pass filter configured to filter the comparison.

19. The device of claim 18, wherein the low-pass filter is configured to reduce transient errors.

20. The device of claim 18, wherein the controller is further configured to compare the filtered comparison to a predetermined threshold.

21. The device of claim 20, wherein the controller is further configured to indicate the developing fault when the filtered comparison exceeds the predetermined threshold for a specified amount of time.

22. The device of claim 12, wherein the controller is further configured to activate an alert and/or place the device into a service required mode when the developing fault is detected.

23. The device of claim 12, wherein the comparison is a difference between the load motor torque value and the input motor torque value, the difference being associated with losses in the motor.

24. The device of claim 23, wherein the controller is further configured to compare the difference to a predetermined threshold.

25. The device of claim 24, wherein the controller is further configured to indicate the developing fault when the difference exceeds the predetermined threshold for a specified amount of time.

26. The device of claim 12, wherein the controller is configured to instruct the motor to correct for variations in ambient pressure and/or temperature.

27. The device of claim 12, wherein turbine-based ventilator is a flow-target, volume-target, and/or pressure-target device.

28. The device of claim 12, wherein the turbine-based ventilator device is a PAP device.

* * * * *